(12) United States Patent
Slembrouck et al.

(10) Patent No.: US 8,701,596 B2
(45) Date of Patent: Apr. 22, 2014

(54) **METHOD FOR THE MASS PRODUCTION OF *CHROMOBOTIA MACRACANTHUS***

(75) Inventors: Jacques Slembrouck, Jakarta (ID); Marc Legendre, Saint-Clement de Riviere (FR); Laurent Pouyaud, Le Triadou (FR); Darti Satyani, Jakarta (ID); Ketut Sugama, Jakarta (ID)

(73) Assignees: Institut de la Recherche pour le Development (I.R.D.), Marseilles (FR); Agency for Marine and Fisheries Research and Development Ministry of Marine Affairs and Fisheries, Jakarta (ID)

( * ) Notice: Subject to any disclaimer, the term of this patent is extended or adjusted under 35 U.S.C. 154(b) by 641 days.

(21) Appl. No.: 12/935,288

(22) PCT Filed: Apr. 2, 2008

(86) PCT No.: PCT/FR2008/000450
§ 371 (c)(1),
(2), (4) Date: Feb. 22, 2011

(87) PCT Pub. No.: WO2009/122019
PCT Pub. Date: Oct. 8, 2009

(65) Prior Publication Data
US 2011/0132271 A1 Jun. 9, 2011

(51) Int. Cl.
*A01K 61/00* (2006.01)

(52) U.S. Cl.
USPC .................................................. 119/217

(58) Field of Classification Search
USPC ................... 119/200, 215, 217, 218
See application file for complete search history.

(56) References Cited

U.S. PATENT DOCUMENTS 3,741,158 A * 6/1973 Moe et al. ............... 119/217
4,697,546 A * 10/1987 Chrisman et al. ........ 119/217

OTHER PUBLICATIONS

Journal of Applied Ichtyology, 1999, pp. 49-53, vol. 15, Blackwell Wissenschafts-Verlag, Berlin, XP002515280.
Newton Castagnoli, Edward M.Donaldson: "induced Ovulation and Rearing of the Pacu (*Colossoma mitrei*)", Aquaculture, 1981, pp. 275-279, vol. 25, Elsevier Scientific Publishing Company, Amsterdam, XP002515281.
Schiavone R., Zilli L., Vilella S., Fauvel C. :Aquaculture, 2006, pp. 522-531, No. 255, XP025041092.
International Search Report, Dated Mar. 12, 2009, in PCT/FR2008/000450.

* cited by examiner

*Primary Examiner* — Rob Swiatek
*Assistant Examiner* — Danielle Clerkley
(74) *Attorney, Agent, or Firm* — Young & Thompson (57) ABSTRACT

A method for the mass production of fish belonging to the order of Cypriniforms, notably to the family of Cobitidae, from spawners which are raised in closed circuit.

7 Claims, 9 Drawing Sheets

Development of *Chromobotia macracanthus* larvae from hatching to the age of 31 days.

FIGURE 1

Variation in the percentage of females undergoing vitellogenesis (Stage 3) and at end of vitellogenesis (Stage 4) belonging to *C. macracanthus* from Sumatra (A) and Kalimantan (B) as kept in captivity in a closed circuit

FIGURE 2

Variation in the percentage of males undergoing sexual maturation (Stage 1) and of males (Stages 2 and 3) belonging to *C. macracanthus* from Sumatra (A) and Kalimantan (B) as kept in captivity in a closed circuit

FIGURE 3

Average variation in the oocyte modal diameter of 2 *C. macracanthus* females as isolated at 25-26°C and of 2 others at 30-31°C.

FIGURE 4

Percentage ovulation obtained after hormone treatment according to the initial modal diameter of oocytes.

FIGURE 5

Relationship between lag time after hormone treatment and housing water temperature for *Chromobotia macracanthus* spawners

A : females treated with two successive injections of Ovaprim

B : females treated with one hCG injection followed by one injection of Ovaprim.

FIGURE 6

Influence of egg agitation on the quality of egg incubation with *C. macracanthus*

FIGURE 7

Model funnel-shaped fiberglass incubator

FIGURE 8

Influence of incubation temperature on the hatching percentage (A) and the proportion of viable larvae with *C. macracanthus* (B)

FIGURE 9

Development of *Chromobotia macracanthus* larvae from hatching to the age of 31 days.

METHOD FOR THE MASS PRODUCTION OF *CHROMOBOTIA MACRACANTHUS*

This invention relates to a method for the mass production of fish belonging to the order of Cypriniforms, notably to the family of Cobitidae, in particular *Chromobotia macracanthus*.

In 1996, the value of exports for fish and ornamental invertebrates was more than $200 million, of which over 60 percent (or some $130 million) went to developing countries. Since 1985 international trade in ornamental aquatic organisms has been increasing on average by 14 percent annually. Those organisms which are caught as wild animals only represent a small percentage of the total trade in ornamental animals. But it is this aspect of the industry which will probably have the greatest impact on fishermen communities in developing countries.

Asia and South America are the main suppliers of ornamental fish in the world, whereas the United States, Europe and Japan are the principal importers. In 1998 the aquarium fish industry in South-East Asia was estimated at $150-200 million, and Singapore, by far the main exporting country, sold between $80-90 million. These figures are low estimates, and it is said that the true figures amount to over $300-400 million for South-East Asia only. Production in Singapore is largely based on the reconditioning of fish from neighbouring countries such as Indonesia, Malaysia, Ceylon (Sri Lanka) and Thailand.

Although part of the Indonesian production goes through Singapore, the export of aquatic organisms from Indonesia is officially $13.4 million, which made Indonesia the $4^{th}$ world exporter in 2004. However, the value as given by Indonesian airport quarantine agencies is $130 million. According to the Ministry of Maritime Affairs and Fisheries the country has 48,000 small and larger producers of fresh water ornamental fish, producing over 60 million fish a year. Many among these producers are anxious to obtain a reliable production system for *Chromobotia macracanthus*.

*Chromobotia macracanthus* (Bleeker) is classified in <<Category 1>> in the fresh water ornamental fish industry in South-East Asia. A native fish of Indonesia, and caught in the rivers of Sumatra and Kalimantan, *C. macracanthus* is an export item to all continents. Being sold between 6-8£ (or more) in Europe, it had an estimated international market in 1998 of 20 million units, measuring 3-8 cm, as exported from Indonesia. This figure is apparently highly underestimated, and international demand increases regularly. These estimates only pertain to the number of exported animals, and do not take into account loss after harvest (diseases, stress, etc.) or damage incurred (habitat, other aquatic species also caught). Industry specialists note a regular decrease in the number of juvenile fish caught, albeit fished with increasing intensity for almost 30 years. It is clear that this species is overexploited and threatened, which brought the Indonesian government to forbid, in a 2002 Decree, the export of fish above 15 cm, considered sexually mature. The aim of this Decree is to protect spawners in their natural environment.

If during the next decades international demand cannot be satisfied with juvenile fish from fish-rearing farms, *C. macracanthus* will disappear with the corresponding industry, whereas the production of this fish represents an important income locally for rural communities.

Moreover at the international level industry specialists are more and more concerned and constrained by international environment protection standards, and over 80% of species now found on the market come from fish farms.

Controlling the production cycle for this species is therefore an international issue, and artificial reproduction of *C. macracanthus* in captivity seems to have been occasionally obtained in Thailand, in Malaysia, in the Czech Republic, in Russia and in Florida, but this has not been confirmed by any report or article, and no corresponding technical support is available.

In 2005, although Indonesian research institutes had been trying to control the reproduction cycle of *C. macracanthus* for more than 10 years (Satyani D. (2004) Journ. Penel. Perik. Indon. 10(5), p. 55-59; Satyani D., H. Mundriyanto, T. Kadarini dan Kusdiarti 2005 Prosiding Seminar Nasional dan Konggres Biologi XIII. Fakultas Biologi UGM. Yogyakarta, p. 435-438; Subandiyah S. (2005) Prosiding Seminar Nasional dan Konggres Biologi XIII. Fakultas Biologi UGM. Yogyakarta p. 290-293; Subandiyah S. dan D. Satyani (2004) Prosiding Seminar Biologi menuju Millenium III. Fakultas Biologi UGM. Yogyakarta p. 127-136), no technical production path had been established. Research work on maturation in the natural environment, on the stimulation and improvement of sexual maturation in captivity has been carried out by using hormone implants, testing enriched or natural foods, and varying the photoperiod, Satyani D., Chumaidi dan Kusdiarti. (2006) Pros. Sem. Nas. Pengembangan Tekn. Budidaya Perikanan dan Temu Bisnis Kerapu. Balai Besar Riset Perik. Budidaya Laut Gondol dan Balai Riset Perik. Air Payau, Maros. PRPB-BRKP. Bali. 111; Subandiyah S. (2005) Prosiding Seminar nasional Perikanan Indonesia. STP. Jakarta p. 185-192; Chumaidi. (2005) Prosiding Sem Nasional Tahunan Hasil Penel. Perik. dan Kelautan. UGM. Yogyakarta p. 249-254; Effendi I., T. Prasetya, A. O. Sudrajat, N. Suhenda and K. Sumawidjaja (2003) Jurnal Akuakultur Indonesia, 2(2), p. 51-54; Satyani D., T. Kadarini dan O. Komarudin (1999) Journ. Penel. Perik. Indon. II (4), p. 37-42; Subagja J., O. Komarudin dan J. Effendi. (1997) Jurn. Penel. Perik. Indon. III (2), p. 10-17).

However at the end of these investigations spawners of *C. macracanthus* when maintained in captivity still find it difficult to reach full sexual maturation. The result is uncertain, of short duration and depends upon climate fluctuations. Although fertilized eggs have sometimes been obtained after hormone induction of ovulation, results have remained difficult to reproduce, and no significant production of fries has been obtained. The production cycle is still a failure, and the amount of ova which is collected is smaller that that obtained in the natural environment. Fertilization rates are very low, over 70% of eggs die during incubation, and 100% of larvae die between 5-9 days after hatching.

There is therefore an important need for a production method of *C. macracanthus* juveniles which would be easily available, reliable, reproducible, and which could allow one to obtain high fertilization rates as well as high survival rates for eggs and larvae.

During their research the inventors found husbandry conditions which allow one to solve all these problems, and they developed a reliable and reproducible method allowing one to obtain high fertilization rates as well as high survival rates for eggs and larvae.

Therefore the invention relates to a method for the mass production of fish belonging to the order of Cypriniforms, notably to the family of Cobitidae, in a closed circuit husbandry structure, comprising the following steps:

a) half-light raising of male and female spawners at a density between 5-15 fish per cubic meter, advantageously between 6-7 fish per cubic meter, in a husbandry tray fed with water at a temperature which is maintained between 30-32° C. during a period between 6-15 months, advantageously during 14 months, then at a lower temperature of 25-29° C., advantageously 25-26° C., this value being maintained during a period between 1-6 months, advantageously 3 months, the spawners being fed during the whole duration of the husbandry period, in the morning with mixed feed given at a rate of 0.5-1% of fish biomass, and in the evening with earthworms representing at least 10% of fish biomass, advantageously 10-15% of said biomass, b) selection of female spawners with an ovocyte diameter between 1.00-1.32 mm, c) selection of male spawners with a good sperm flow after abdominal massage (Sexual maturity Stage 3), d) hormone treatment of female spawners,
   either with two injections of a combination of gonadoliberine, whether purified or in the form of synthetic analogues, and of an anti-dopaminergic compound, said injections being made at 5-8 hrs intervals, advantageously 6 hours, the doses for the first injection being between 2-10 mg/kg, advantageously 8 mg/kg for gonadoliberine and its synthetic analogues, and between 1-5 mg, advantageously 4 mg for the antidopaminergic compound, and the doses for the second injection being between 8-12 mg/kg, advantageously 12 mg/kg for gonadoliberine, whether purified or in the form of synthetic analogues, and between 4-6 mg, advantageously 6 mg for the antidopaminergic compound,
   or with a first injection of human chorionic gonadotropin hormone (hCG) at a rate of 250-500 IU/kg, advantageously at a rate of 500 IU/kg, followed, after 18-26 hours, by a second injection of a combination of gonadoliberine, whether purified or in the form of a synthetic analogue and of an anti-dopaminergic compound at a dose between 4-12 mg/kg, advantageously of 12 mg/kg for gonadotropin, whether purified or in the form of synthetic analogues, and at a dose between 2-6 mg/kg, advantageously of 6 mg/kg for the antidopaminergic compound, e) hormone treatment of male spawners with the injection of a combination of gonadoliberine, whether purified or in the form of a synthetic analogue, and of an anti-dopaminergic compound, at a dose between 2-10 mg/kg, advantageously of 8 mg/kg for gonadotropin, whether purified or in the form of synthetic analogues, and at a dose between 1-5 mg/kg, advantageously of 4 mg/kg for the antidopaminergic compound, f) ovule collection through abdominal massage of female spawners, this being carried out with an average lag time (time duration between injections and ovule collection) which may vary with the temperature of the spawners housing water during the lag time between the hormone treatment and ovulation (between 24-31° C., but advantageously between 26-28° C.) and with the nature of the hormone treatment which is used, following the relationships given herebelow:
   for the treatment with two successive injections of gonadoliberin, as associated with an antidopaminergic compound:

$Y$(Lag time in hours)$=413.97-29.47X+0.54X^2$
($R^2=0.670$), with X=temperature in degrees Celsius
for the treatment with a hCG injection followed by an injection of gonadoliberine as associated with an anti-dopaminergic compound:

$Y$(Lag time in hours)$=771.51-54.08X+0.96X^2$;
($R^2=0.652$), with X=temperature in degrees Celsius g) sperm collection with male spawners 10-48 hrs after hormone treatment, advantageously 12-24 hrs, directly in an immobilisation solution for spermatozoids, advantageously a saline solution (NaCl 0.9%), and preservation in the cold, advantageously at 4° C., h) in vitro fertilization of the eggs, i) incubation of the eggs with slight agitation at a temperature between 24-28° C., advantageously at 26° C. until hatching, j) collection of larvae, k) raising of larvae until the juvenile stage.

The order of Cypriniforms includes the family of Balitoridae, the family of Catostomidae, the family of Cobitidae, the family of Cyprinidae, the family of Gyrinocheilidae and the family of Psilorhynchidae. In an advantageous embodiment of the invention the method relates to the raising of Cobitidae, particularly of *Chromobotia macracanthus*, notably obtained from populations of animals living in Sumatra and Borneo (Kalimantan).

Half-light refers to conditions wherein luminosity is between 0-20 Lux, advantageously between 5-10 Lux; thus spawners may be raised in pools which are partially covered, or in a closed environment with photographic printing laboratory-type red lighting.

According to the invention the fish are subjected in the morning to art known conventional feed; they may be notably nourished 6 days a week in the morning with mixed feed comprising for instance between 35-45% proteins and between 5-15% lipids; the choice of a feed pertaining to the knowledge of an art specialist, he is able to adapt this feed if necessary. The inclusion of earthworms in the evening is an essential element for obtaining good spawners.

In stages b) and c) of the inventive method the fish are advantageously placed in small housing structures (e.g. 150-300 L trays) in order to make handling easier during hormone treatment and during gamete collection, At the end of stage f) the ovae are kept until fertilization under conventional conditions, notably during a period which does not exceed 10 minutes at a temperature between 25-28° C.

The preservation of spermatozoids in the cold at the end of step g) allows their use after a few hours.

In an advantageous embodiment of the inventive method gonadoliberine synthetic analogues are chosen among the group comprising GnRHa (advantageously D-Arg6, Trp7, Leu8, Pro9, Net) or LHRH-A, and the antidopaminergic compound among the group comprising domperidone and pimozide.

In another advantageous embodiment of the inventive method the water which is used is recycled water circulating at a flow rate between 80%-100% husbandry volume water renewal per hour. The water which is used advantageously has a pH between 7.0-8.0, a conductivity between 100-300 μS/cm, and its oxygen concentration is between 6.0-8.0 mg/L.

In another advantageous embodiment of the inventive method the egg incubation step in Stage i) is carried out under moderate agitation conditions as obtained either by an agitation of the eggs in a flow of water, advantageously in a funnel-shaped incubator comprising a bottom water inflow opening in the narrow part of the funnel, said water inflow opening having a diameter between 20-30 mm to allow a water flow rate between 0.3 L·mn$^{-1}$-2.3 L·mn$^{-1}$, or in non-renewal water containers placed on an oscillating tray with 56-88 oscillations per minute around an angle having a total amplitude of 10 degrees (+5, −5). A moderate agitation is one which is sufficiently strong to maintain the eggs in motion, but sufficiently weak to avoid inducing any developmental anomaly or rupture of the chorion.

Thus the inventive method comprises 3 basic stages:
1—a gradual maturation step, or construction step, of the gonads, which may be obtained at a comparatively high water temperature, advantageously between 30-32° C.,
2—a regressive step in sexual maturation, if the fish are maintained in hot water (≥30° C.) during a prolonged period,
3—a stimulation of the development of the gonads (towards the end of the vitellogenesis) through lowering of the temperature to 25-26° C.

Apart from the water temperature a correct feed management (highly abundant earthworm input), and maintaining a good water quality are essential factors for the good health of spawners and their ability to carry out their gonadic maturation.

The inventive method has the following advantages:
1. Spawner husbandry systems and conditions, notably *C. macracanthus* spawners, allowing a high survival rate and a good sexual maturation of these captive fish;
2. Objective criteria for the selection of spawners which are able to react to a treatment for inducing reproduction;
3. Efficient hormone treatments allowing one to induce the final oocyte maturation and ovulation in the females, and to stimulate male spermiation;
4. A definition of the reaction time towards hormone treatments and collection and preservation protocols for ovae and spermatozoa;
5. Reliable modes of egg incubation after artificial fertilization, allowing one to obtain high hatching percentages, with a high proportion of viable larvae,
6. Husbandry conditions for larvae which allow one to obtain high survival rates after 1 month, an age at which the fish are placed into a pre-enlarging structure.

Obtaining a low, or zero, average hatching rate after inducing ovulation was still a major problem for controlling the reproduction of *C. macracanthus* under husbandry conditions. Indeed until 2006, in spite of the fact that satisfying ovulation rates and fertilized egg percentages had been obtained, the average hatching rate was generally very low (26.5%±25.2%) after the egg incubation step, with a very high proportion of abnormal larvae, or on average 57.6±25.2%.

Since then, research carried out by the inventors on this key step in the control of the reproduction of *C. macracanthus* as a captive animal has shown the importance of two main factors on the survival of eggs and embryos: egg agitation, and the incubation water temperature.

Examples 1-5 and FIGS. 1-9 herebelow illustrate the invention.

FIG. 5 represents the relationship between the lag time after hormone treatment and the housing water temperature for spawners of *Chromobotia macracanthus*. A: females treated with two successive injections of Ovaprim®; B: females treated with one injection of hCG followed by an injection of Ovaprim® (Light circles: females from Sumatra; dark circles: females from Kalimantan; Triangles: females from Sumatra for whom the oocyte maturation process has been initiated following the first injection of Ovaprim®)

EXAMPLE 1

Husbandry Conditions and Sexual Maturation of Spawners 1.1. Husbandry Conditions In order to be able to study the parameters which influence the sexual maturation of captive *C. macracanthus*, closed circuit husbandry structures which are adapted to the maintenance of this species were designed and constructed at Depok station (Indonesia). *C. macracanthus* spawners from Sumatra (N=66; 70% female) and a group from Kalimantan (N=59; 75% female) were raised with a density of 6-7 fish per cubic meter.

Each husbandry tray (10 m$^3$) is fed with recycled water (flow rate=8.2 m$^3 \cdot$hr$^{-1}$) with a mechanical filter, a biological filter, and a U.V. lamp (sterilization). In order to reduce stress, the fish are isolated in a dark room. This thermally isolated room also allows one to regulate temperature all the year long at a level which is chosen between 25° C. and 32° C. Each closed circuit is fed with drilling water. Being oversaturated with gas this water must beforehand be aerated during 24 hrs before it can be used for raising fish. Monthly water temperature values fluctuated between 30-32° C. during 14 months, then temperature was adjusted at 26-27° C. during 6 months.

The fish were fed 6 days a week; in the morning artificial granule feed was given at a rate of 0.5-1% of biomass, and in the evening feeding was carried out with earthworms according to demand (input >10% of fish biomass). The husbandry pools were siphoned twice a week with a weekly fresh water input of 10%.

1.2. Results

Figure 1:
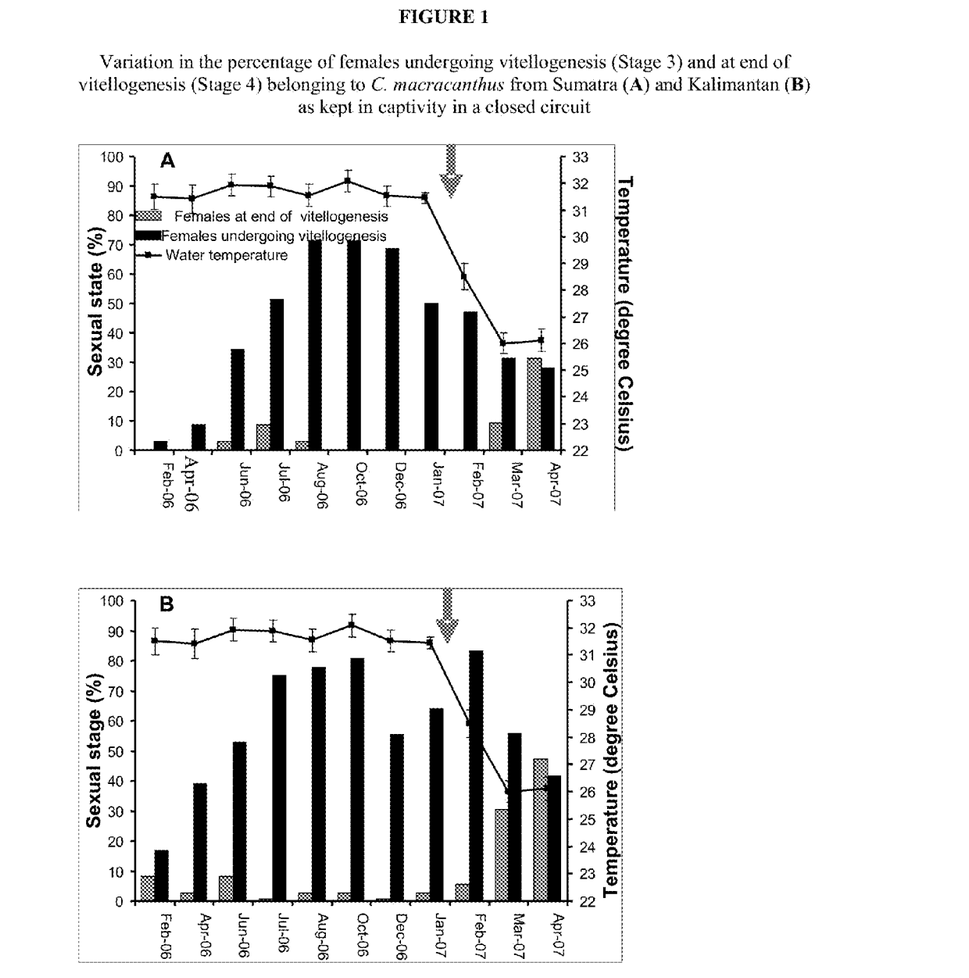
FIG. 1 represents the variation, following the water temperature, in the percentage of females undergoing vitellogenesis (Stage 3) and after vitellogenesis (Stage 4) of *C. macracanthus* from Sumatra (A) and Kalimantan (B), as maintained in captivity in a closed circuit under the conditions of Example 1.
Figure 2:
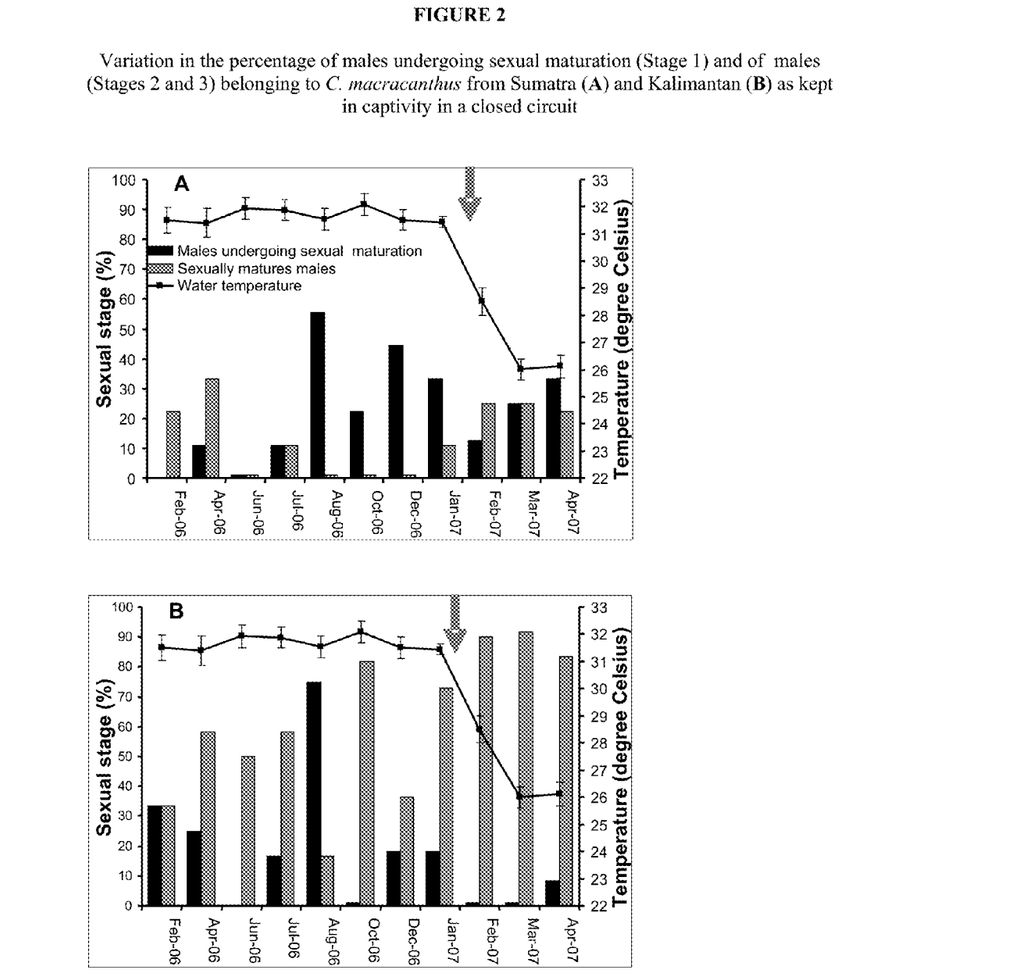
FIG. 2 represents the variation, following the water temperature, in the percentage of males during sexual maturation (Stage 1) and of male animals (Stages 2 and 3) of *C. macracanthus* from Sumatra (A) and Kalimantan (B), as maintained in captivity in a closed circuit.
Figure 3:
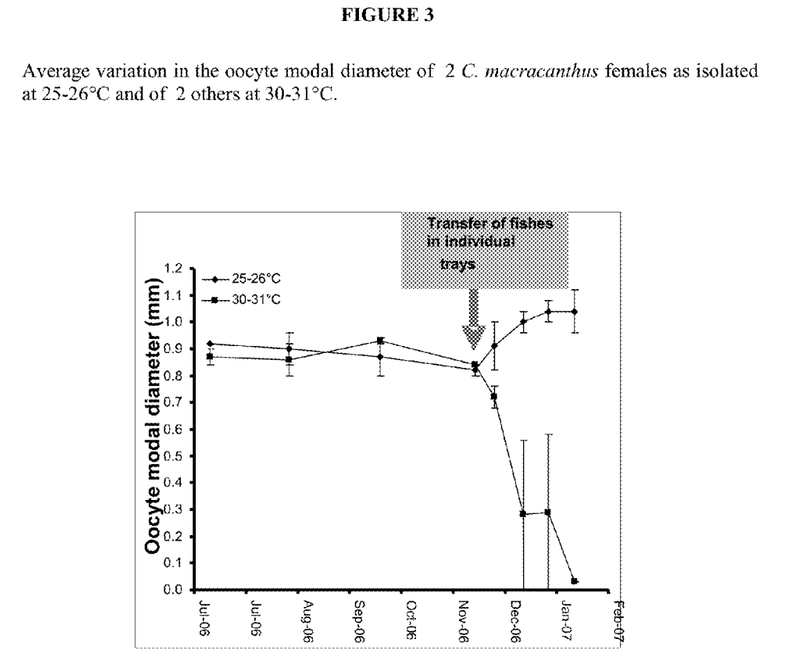
FIG. 3 represents the average variation in the ovocyte modal diameter of 2 *C. macracanthus* females as isolated at 25-26° C., and of 2 more at 30-31° C. After having been raised in the same pool with recycled water at 30-31° C., the four females are isolated in identical trays (250 L) which are thermoregulated at the chosen temperatures.

They are illustrated in FIGS. 1-3.

After the fish had been raised for 20 months the main physicochemical parameters of the water in the husbandry units were still below toxic standard levels for *C. macracan-* thus spawners; pH was between 7.1-7.7; conductivity varied between 114-294 µS/cm, and the measured oxygen concentration showed little variation
(6.7-8.1 mg·L$^{-1}$). The non ionized ammonia content was between 0.0-0.1 mg·L$^{-1}$, whereas concentrations vary between 0.00-0.03 mg·L$^{-1}$ for nitrites, and between 6.3-20.0 mg·L$^{-1}$ for nitrates.

The feeding method which is used is well adapted for this species, as females are fat and are undergoing sexual maturation (assessment carried out according to the method of Example 2). Under these husbandry conditions it is possible to obtain up to 90% maturating females, with 40-47% of females ready for reproduction. No pathology was found in these farms, and survival has remained above 85%.

Voluntary water temperature fall for raising fish has made it possible to obtain 80-90% of females undergoing sexual maturation after two months at low temperature levels (26-27° C.). Following this voluntary temperature fall the proportion of females ready to hatch has increased from 8 to 50% for fish in the population from Kalimantan, and from 9% to 30% for those from Sumatra (FIG. 1).

Under these husbandry conditions one obtains between 60-90% of males which are sexually mature, that is to say in Stage 3 (FIG. 2). These observations were made between April and July, or in a season which is not the natural reproduction period, the latter being concentrated between September and December in the rivers of Sumatra.

Simultaneously four females in the same sexual stage, after having been raised in the same pool in recycled water at 30-31° C., were isolated in identical trays (250 L) which were thermoregulated at the chosen temperatures of 30° C. or 26° C. After 2 months' observation, oocytes of females placed in a cold temperature environment showed a regular growth and were in the final vitellogenesis stage (reproductive ability), whereas oocytes of females placed in a warm temperature environment regressed completely (FIG. 3).

EXAMPLE 2

Spawner Selection Criteria for the Inductive Treatment of Reproduction 2.1. Method In order to facilitate individual monitoring each spawner is narcotized (in a bath containing 0.3 mL·L$^{-1}$ Phenoxy-2-ethanol), then marked with an electronic tag (PIT Tag) which is inserted in the back muscles with a trocar. Samplings are made every 45-60 days, and the condition of spawners (body weight/length ratio$^3$) as well as their sexual maturation stage are assessed. During each sampling operation all fish are taken, identified, measured and weighed individually, in order to determine the monthly weight increase and to reassess their diet.

The sexual maturation stage of each female is assessed by taking some fifty oocytes by way of intra-ovarian biopsy with a flexible catheter (outer diameter: 2 mm). The oocytes are placed into a saline solution (NaCl 0.9%) and their greater diameter is measured immediately with a binocular magnifier (×25) in order to determine the modal diameter of the most developed oocyte group. Four main sexual maturation stages may be distinguished:

Stage 1: immature females (non canulable).
Stage 2: ovaries with oocytes in pre-vitellogenesis (modal diameter ≤0.4 mm)
Stage 3: Development of the ovary and strong oocyte growth stage, presence of many oocytes in exogenous vitellogenesis phase (0.4 mm<modal diameter<1.02 mm)
Stage 4: presence of a large majority (70-90%) of post-vitellogenic oocytes (modal oocyte diameter ≥1.02 mm), which are able to ovulate after hormone treatment.

The sexual maturity stage of males is determined after the presence and the amount of sperm emitted after abdominal massage of the fish, according to the following arbitrary scale:

Stage 0: no sperm
Stage 1: emission of a small amount of sperm with a sustained abdominal pressure,
Stage 2: presence of sperm in average amount, easy emission during abdominal massage,
Stage 3: abundant sperm, flowing with a slight abdominal pressure.

2.2. Results

Figure 4:
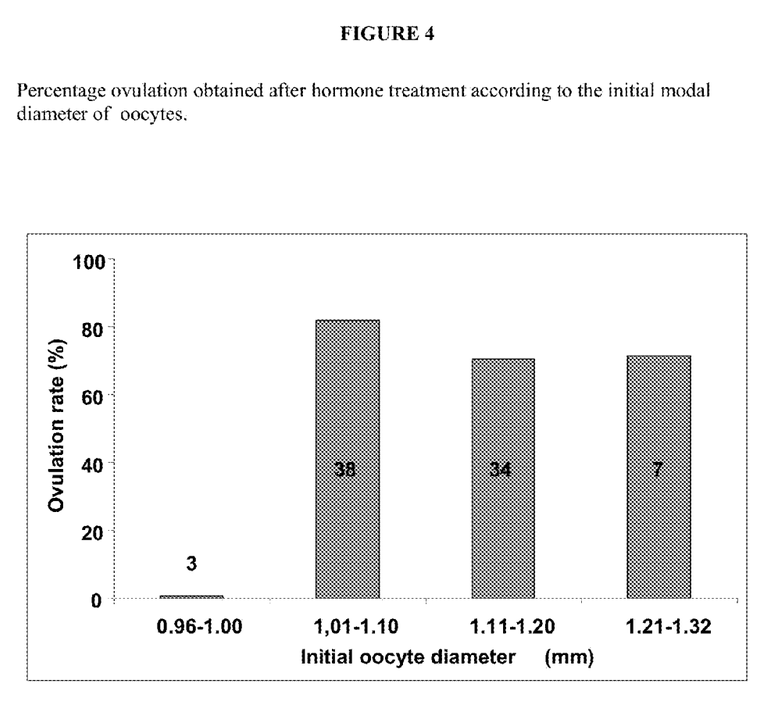
FIG. 4 represents the percentage of ovulation as obtained after an inventive hormone treatment according to the initial modal diameter of oocytes. The results are overall results for the two types of hormone treatments.

They are given in FIG. 4 and Table 1.

After an intra-ovarien biopsy, the females used for induced reproduction were selected on the basis of their fatness and of a modal oocyte diameter ≥1.02 mm, a minimum modal oocyte diameter from which ovulation may be successfully induced with C. macracanthus after hormone treatment. (FIG. 4). Fatness in the females (rounded appearance of belly) is a second rank criterion allowing one to refine the selection of females for reproduction. It is assessed according to a subjective scale along 3 levels: 0—no particular fatness in the female, 1—abdomen notably rounded, 2—abdomen highly rounded. Indeed females with a rounded abdomen allow one to obtain a significantly higher amount of ova as compared with those with no marked fatness (p<0.05), and the ovulation rate also tends to be higher (p>0.05). On the other hand there is no marked difference between the two groups of females (Table 1).

TABLE 1

Comparison of ovulatory responses and of amounts (fertility) and quality (fertilization) of collected ova after hormone treatment (with preparatory hCG injection) among females of C. macracanthus according to their initial fatness (average ± sd).

| Fatness | Ovulatory response (%) | Fertility (n/kg female) | Fertilization (%) | Numbers |
| --- | --- | --- | --- | --- |
| Absent | 56 | 54,576 ± 29,240 | 63 ± 31 | 9 |
| Notable or high | 70 | 120,730 ± 38,250 | 61 ± 16 | 10 |

Thus the modal oocyte diameter, as determined after intraovarian biopsy, allows one to assess the ability of oocytes to respond to the hormone treatment which is carried out to obtain ovulation. The female's fatness, on its part, is seen as an indicator of the amount of ova which may be collected after ovulation. However the sole use of this second criterion would not be sufficiently reliable, because fatness may also have other causes than the development of the gonad (notably the amount of perivisceral fat, or of feed intake).

EXAMPLE 3

Hormone Treatments and Management of Collected Gametes 3.1. Method

Like the vast majority of teleostian fishes, *Chromobotia macracanthus* does not breed spontaneously when in captivity (however some egg-laying has been observed in aquariums), although it is able to undergo its gonad maturation in that environment. One must therefore carry out a hormone treatment to induce the final maturation of oocytes and ovulation. Among males the hormone treatment makes it possible to increase the amount of sperm which is collected and to make this collection easier because the viscosity of the semen is reduced.

As to the females, two hormone treatments have proved to be efficient. The first treatment consists in two injections of Ovaprim®, separated by a time lag of 6 hrs, and at the respective doses of 0.4, then 0.6 mL/kg. The second treatment corresponds to a first injection of hCG (Human Chorionic Gonadotropin) at a rate of 500 UI·kg$^{-1}$, this being followed, 24 hrs later, by an injection of Ovaprim® at a rate of 0.6 mL/kg. For these two treatments, the time lag between the second hormone injection and the ovulation (as detected by the possible collection of ova through an abdominal massage of the females) was compared with the fish housed at various temperatures.

The males are chosen at Stage 3 of sexual maturity, and only receive one injection of Ovaprim® at a dose of 0.4 mL/kg. The sperm, as collected with an abdominal massage between 16-24 hrs after hormone treatment, is directly collected in a syringe containing a NaCl 155 mM solution (1 volume for 4 volumes) in order to avoid any possible activation of spermatozoa due to a contamination of the sperm with urine, then kept at 5° C. before being used for fertilization.

Once an ovulation has been detected (to this end each female is examined several times at 1 or 2 hrs intervals), the ova are collected through abdominal massage, then weighed and fertilized with sperm from several males.

The quality of each female's ova is assessed with the fertilization and hatching rates as obtained from replicated experimental batches, each comprising ca. 150 eggs which were incubated in small plastic containers having a water capacity of 300 mL. The in vitro fertilization method of these experimental egg batches is the following: ca. 150 ova are placed in a plastic container, 100 μL sperm as diluted in the saline solution are added onto the ova, then the spermatozoid motility is activated by adding 10 mL water. Once the water is added the eggs are agitated with care during 1 minute in order to allow fertilization. The water and the sperm are then eliminated and the eggs are rinsed with clean water before being incubated. All experimental incubations are made with spring water under standardized conditions. For mass larvae production trials the remaining eggs of each female are fertilized and incubated in recycled water in a fish hatchery.

The efficiency of these hormone treatments was assessed on 62 females having undergone their sexual maturation under satisfying conditions, as concerns their feed as well as the quality of the water.

The fish used for these experiments belonged to 3 separate groups:

39 females from Sumatra, who were directly caught, in full sexual maturity, in the Musi river (South Sumatra province), then temporarily kept in floating cages. Their reproduction was induced less than 10 days after being caught, either on site near the river, or after transportation by plane and car to Depok experimental station. Thus this group corresponds to individuals having undergone their gonad maturation under natural conditions in the river.

14 females belonging to the same population as the preceding ones (Musi River, Sumatra), but which were raised in thermoregulated closed circuit at Depok station during more than one year before the reproduction tests were induced, and 9 females from a different population, originating from the island of Borneo (Indonesian Kalimantan province), and raised in a thermoregulated closed circuit, under the same conditions as the females from Sumatra.

3.2. Results

It must also be noted that for the fish which were kept under husbandry conditions in half-light in a closed circuit, the half-light and the care given by bench scientists made it possible to restrict stress factors.

The obtained results demonstrate the efficiency of the hormone treatments as chosen to induce ovulation. No significant difference was shown between the two hormone treatments which were used, whether in terms of the obtained ovulatory response, or of the amount and quality of ova as collected.

Figure 5:
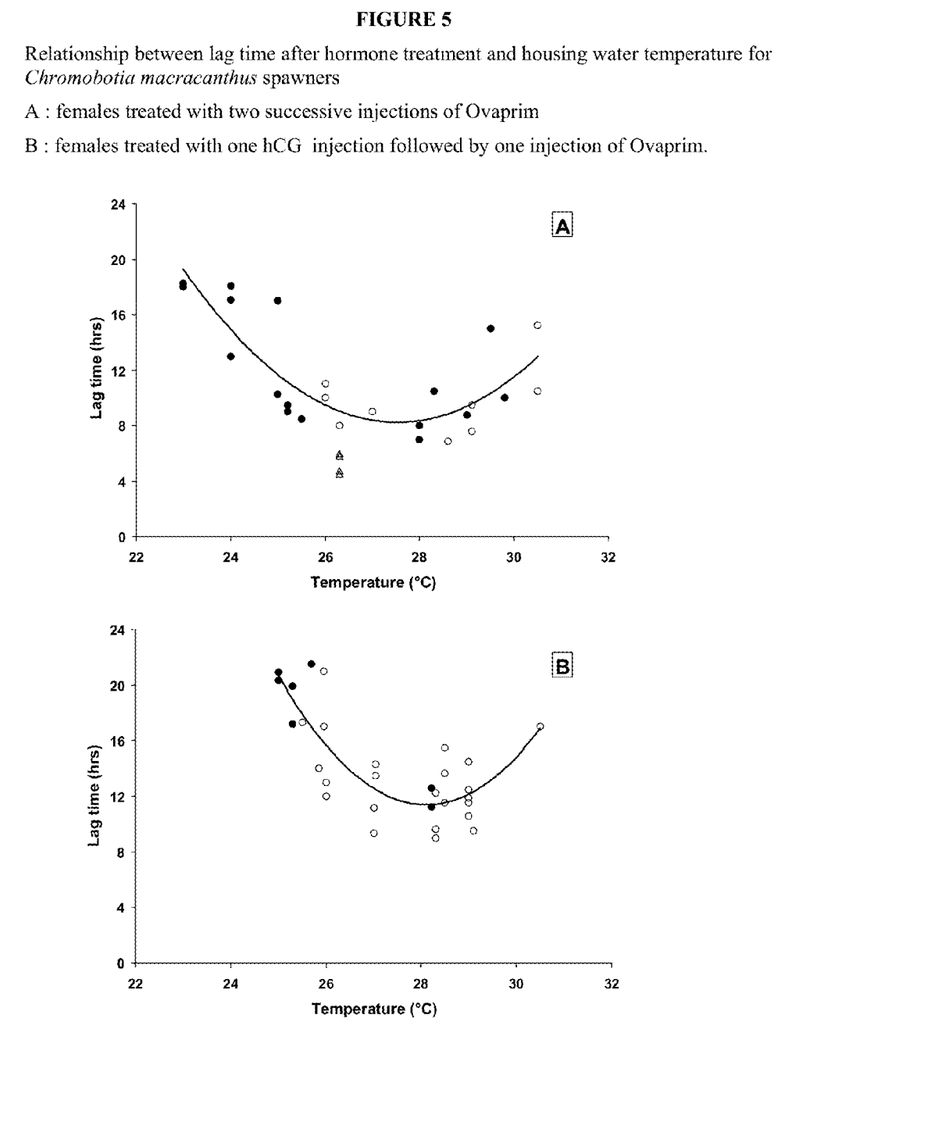

The variation in lag time (time between the second hormone injection for ovulation) following the housing temperature for spawners, as tested between 23° C.-30.5° C., shows a relationship which is quite unusual among fish. Indeed this relationship, which is usually nearly linear (with the lag time decreasing with temperature according to a log-linear relationship) is now in the form of a second degree polynomial, whatever hormone treatment is being considered (FIG. 5). The relationships are highly significant for all of their terms. The corresponding equations are the following (Y=lag time in hrs and X=T=temperature in ° C.):

Treatment with two successive injections of Ovaprim®:

$$Y=413.97-29.47X+0.54X^2; R^2=0.670$$

Treatment with one injection of hCG followed by one injection of Ovaprim®:

$$Y=771.51-54.08X+0.96X^2; R^2=0.652$$

Informations pertaining to the study of the ecology of this species in a natural environment, to which one must add the experimental studies of the effect of temperature on the success of egg incubation, show that a temperature interval of ca. 26-28° C. is an optimum for the reproduction of this species. At this temperature the lag time is about 4 hrs longer with the hCG+Ovaprim® treatment, as compared with the Ovaprim®+Ovaprim® treatment. The more one moves away from this temperature interval towards lower or higher temperature levels, the more rapidly does the lag time increase. Towards lower temperature levels this lag time increase is not surprising as it corresponds, at least partly, to a slowing down of the metabolism with these poikilothermic organisms. On the other hand the lag time increase towards higher temperature levels is a paradox, considering one should expect an acceleration of the metabolism, and therefore a decrease in the lag time, as has been reported with many teleostian fish species. The physiological mechanisms underlying this paradoxical response have not yet been identified, and must be the subject of further studies. However it seems that the species does not breed naturally in waters with temperatures above 28.0° C. where this reproduction would be doomed, considering the death rate of embryos.

The ovulation rates which were obtained, or between 78-82%, are systematically high for the females in the three populations under test (Table 2).

The amounts of ova which are collected are also high, and correspond to an average ratio of 8%, 9% and 6% of the female weight, for the two populations from Sumatra and Kalimantan, respectively. These high average gonado-somatic ratios point to a complete ovulatory response, induced by the hormone treatments. In other words, almost all postvitellogenic oocytes which are present in the ovary undergo their oocyte maturation, and they ovulate following the hormone treatment. Cases of partial ovulation were only rarely suspected. The corresponding relative fertilities (number of collected ova in relation to the weight of the female) are ca. 10,500 ova for a female from the Sumatra population weighing 100 g. It is very important to underline here that the fertility of the Sumatra females as raised in closed circuit is approximately at the same level as that of the females which have undergone their gonad maturation under natural conditions in the river. This shows that the conditions as hereabove defined for the maintenance of spawners in captivity make it possible for the females to reach full sexual maturity. Although the difference may not be statistically significant, it is to be noted that fertility tends to be lower for females belonging to the original Kalimantan population (Table 2). The quality of the collected ova, as assessed by the fertilization percentage, is quite satisfying for the females belonging to the population from Sumatra (between 61-74% on average). The quality of the ova is lower (34% on average) for the females from the Kalimantan population.

TABLE 2

Ovulatory response, relative fertility and fertilization percentages obtained after hormone treatment for three *C. macracanthus* populations.

| Origin and Maturation conditions for the females | Class size | Ovulatory response (%) | Fertility (n.kg$^{-1}$) | Fertilization (%) |
| --- | --- | --- | --- | --- |
| Sumatra River | 39 | 82 | 103,550 ± 14,125 | 61 ± 5 |
| Sumatra Closed circuit | 14 | 79 | 108,670 ± 14,090 | 74 ± 9 |
| Kalimantan Closed circuit | 9 | 78 | 73,780 ± 11,240 | 34 ± 7 |

EXAMPLE 4

Figure 7:
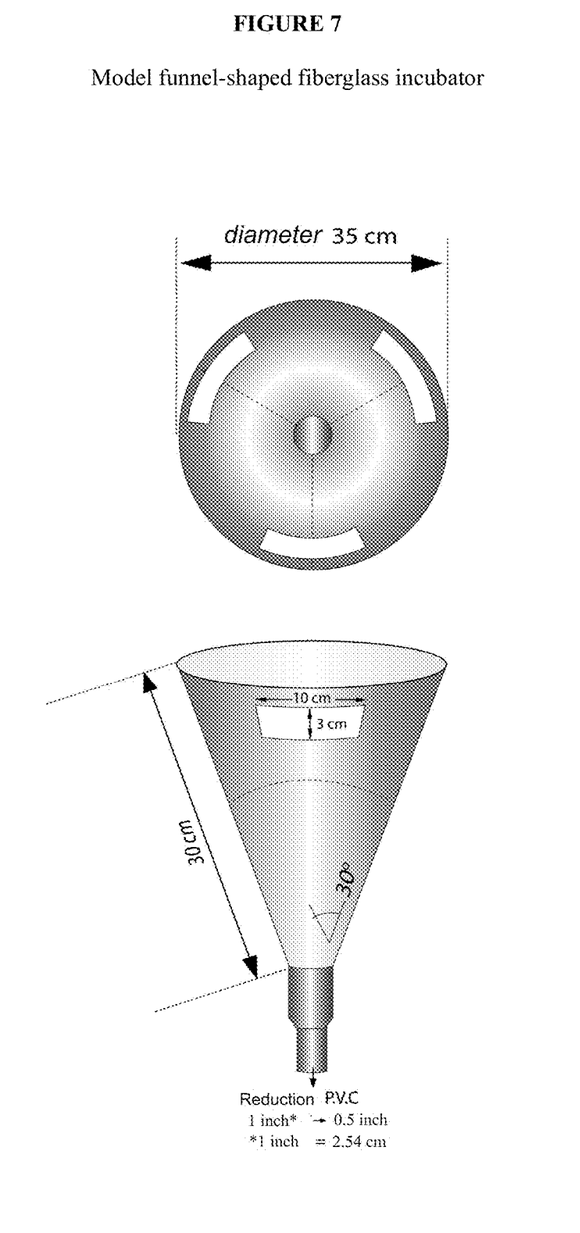
FIG. 7 represents a model funnel-shaped incubator made of fiberglass.

Modes of Egg Incubation after Artificial Fertilization 4.1. Method
4.1.1. Agitation of the Eggs About 150 eggs are either placed in plastic containers containing 300 mL water, and themselves placed upon an oscillating tray, in order to keep the eggs in a permanent motion, or the eggs are placed in a flow of water, thus allowing the eggs to undergo a slow motion without any impacts. But other types of incubators may be functional, and funnel-shaped incubators with a bottom water inlet, allowing one to maintain the eggs in motion in a moderate flow of water have also been used. Importants points in this kind of system are a surface of matter which is sufficiently smooth not to damage the eggs, and a water inlet diameter which is sufficiently wide to yield an efficient flow of water without too high a flow rate when emerging into the incubator. Indeed applying too high a flow rate may lead to a premature bursting of the egg chorion and to the death of the developing embryos. Incubators having the dimensions as indicated in FIG. 7 were tested and seen to yield good results, with an inlet water flow rate of 0.3 L·mn$^{-1}$ and 2.3 L·mn$^{-1}$ L·m$^{-1}$.

At the same time other egg batches were incubated under the same temperature conditions, but in stagnant water.
4.1.2. Influence of the Incubation Temperature Incubation was carried out at various temperatures between 22° C.-30° C., to with 22° C., 24° C., 26° C., 28° C. and 30° C.

4.2. Results
4.2.1. Agitation of the Eggs

Figure 6:
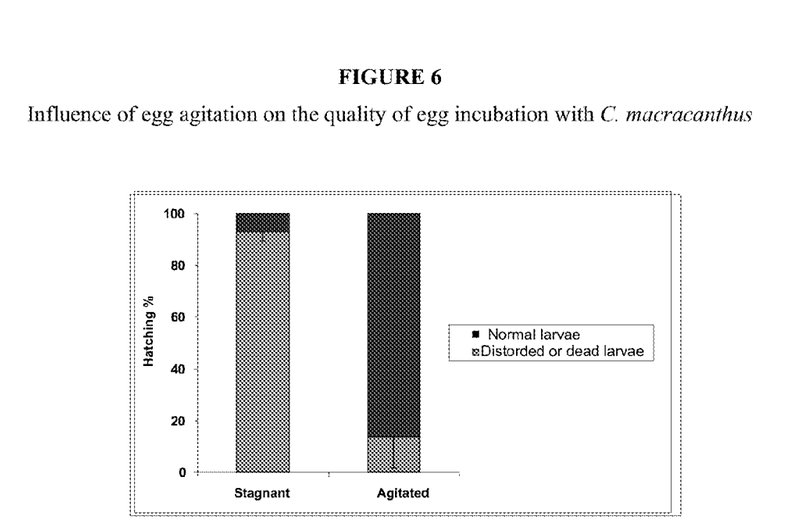
FIG. 6 represents the influence of egg agitation on the quality of egg incubation with *C. macracanthus*.

Results are given in FIG. 6.

Incubation of the eggs in stagnant water leads to an abnormal development of the embryo, as shown by the almost total lack of movements of the embryos at the end of their development, and then by the almost complete mortality rate (over 90%) of the larvae when hatching (FIG. 6).

On the other hand, when incubated under the same conditions on an oscillating tray the eggs develop and hatch normally: over 85% normal larvae, i.e. active and viable ones, are obtained (FIG. 6).

When placed in the water after fertilisation the eggs swell and develop an important perivitelline space (the egg diameter increases by ca. 300%), which gives them a weakly negative buoyancy (thus a weak water flow may lift up the eggs and throw them back into a suspension in the water mass).

Figure 8:
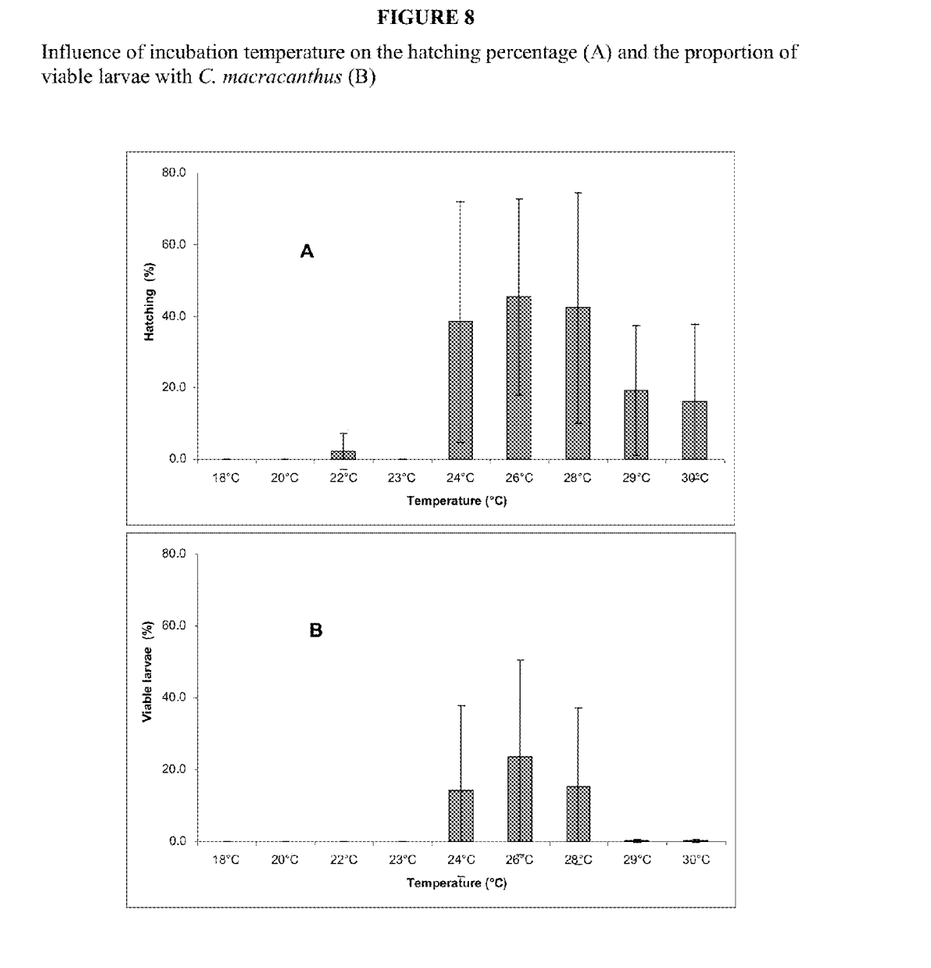
FIG. 8 represents the influence of the incubation temperature on the hatching percentage (A), and the proportion of viable larvae with *C. macracanthus* (B).

Similar results were obtained with an funnel-shaped incubator having a bottom water inlet, allowing one to maintain the eggs in motion in a moderate flow of water (FIG. 7). In this kind of incubator, and under convenient temperature conditions, the obtained average hatching percentage is 75.7±6.2% (n=9 females), with an acceptable proportion of distorted larvae, i.e. on average 17.0±16.5%.
4.2.2. Influence of the Incubation Temperature Results are given in FIG. 8.

Although *C. macracanthus* is a fish species whose geographical distribution is restricted to the tropical fresh waters of the islands of Sumatra and Borneo in Indonesia, our research shows a high sensitivity of the eggs to water temperatures above 28° C. (at which the eggs of most tropical fishes develop normally), as well as to temperatures below 24° C.

Experiments independently carried out on eggs from 9 different females from Sumatra or Kalimantan populations (FIG. 7) show that:
- no hatching is obtained at 18° C. nor at 20° C., with the development of the embryo not going beyond the morula stage;
- at 22-23° C., only a few hatchings of distorted larvae (non viable) may be obtained;
- at 29° C. and 30° C., the obtained average hatching percentages do not exceed 20%. Moreover the obtained larvae show notable distortions, and none of them is viable;
- only the temperature interval between 24° C.-28° C. has made it possible to obtain average hatching percentages above 40%, with a high proportion of larvae which are normal and viable. Although the hatching and normal larvae percentages as obtained at 24° C., 26° C. and 28° C. show no stastistically significant differences the highest values are obtained at 26° C., towards the center of the temperature interval.

Thus a temperature of 26° C. is recommended for the incubation of *C. macracanthus* eggs from Sumatra or Borneo populations.

EXAMPLE 5

Larvae Husbandry Conditions

The raising of larvae is no longer a problem as research conducted by the inventors has shown that under satisfying feeding (*Artemia nauplii* in excess) and water quality (high dissolved oxygen concentration, low concentrations of ammonia and nitrites, neutral pH, temperature 28-

Figure 9:
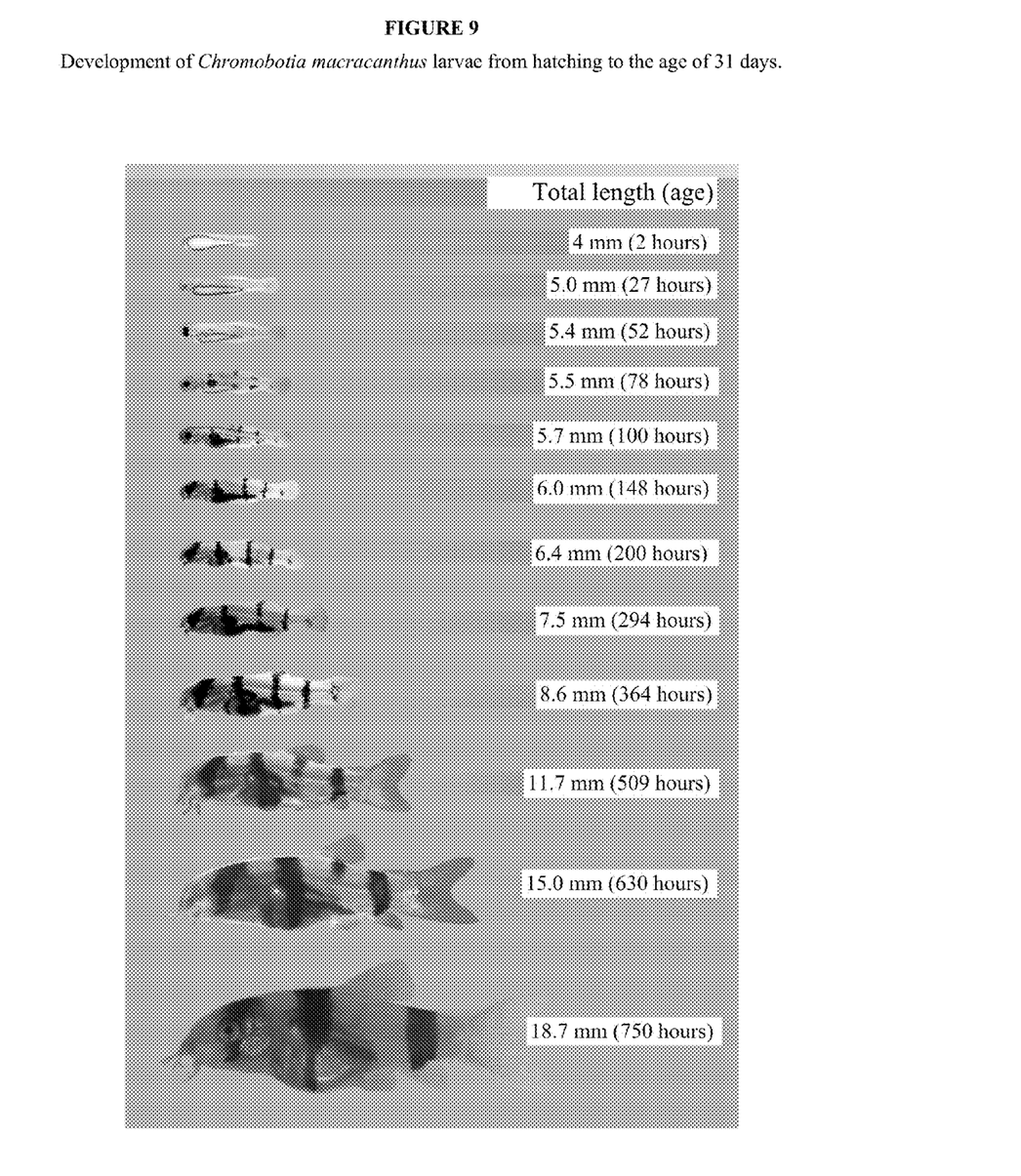
FIG. 9 represents the development of *Chromobotia macracanthus* larvae from hatching to the age of 31 days.

30° C. . . . ) conditions one may obtain survival rates between 60-90% after raising during one month. The juveniles may be marketed after having been raised for two months (FIG. 9).

The invention claimed is:
1. A method for the mass production of fish belonging to the order of Cypriniforms, in a closed circuit husbandry structure, comprising:
   a) half-light raising male and female spawners at a density between 5-15 fish per cubic meter, in a husbandry pool fed with water with a temperature kept between 30-32° C. for a period of time between 6-15 months, whose temperature is then lowered to 25-29° C. and kept at this level for a period of time between 1-6 months, the spawners being fed, during the whole raising period, in the morning with mixed feed distributed at a rate of 0.5-1% of the fish biomass, and in the evening with earthworms representing at least 10% of the fish biomass,
   b) selecting female spawners having an oocyte diameter between 1.00 and 1.32 mm,
   c) selecting male spawners with whom the sperm flows easily by abdominal massage,
   d) hormone treating the female spawners, the hormone treatment comprising one of the following:
      (1) two injections of a combination of gonadoliberine, whether purified or in the form of synthetic analogues, and an anti-dopaminergic compound, said injections being made at 5-8 hour intervals, the doses for the first injection being between 2-10 µg/kg, for the gonadoliberine and its synthetic analogues, and being between 1-5 mg/kg for the antidopaminergic compound, and the doses for the second injection being between 8-12 µg/kg for the gonadoliberine and its synthetic analogues, and between 4-6 mg/kg for the antidopaminergic compound, or
      (2) a first injection of human chorionic gonadotropin hormone (hCG) at a dose of 250-500 IU/kg, the first injection being followed, after 18-26 hours, by a second injection of a combination of gonadoliberine, whether purified or in the form of a synthetic analogue, and an anti-dopaminergic compound, the dose being between 4-12 µg/kg for the gonadoliberine or its synthetic analogues, and the dose being between 2-6 mg/kg for the antidopaminergic compound,
   e) hormone treating the male spawners by injection of a combination of gonadoliberine, whether purified or in the form of a synthetic analogue, and of an anti-dopaminergic compound, at a dose between 2-10 µg/kg for the gonadoliberine or its synthetic analogues, and at a dose between 1-5 mg/kg for the antidopaminergic compound,
   f) collecting ova through abdominal massage of the female spawners, the collecting being carried out with an average lag time Y (hours) between injections and ova collection that varies with the spawner maintenance water temperature of between 24-31° C., and with the hormone treatment that is used, according to the following relationships:
      for the hormone treatment with the two successive injections of the gonadoliberine in combination with the antidopaminergic agent:

$Y(hours) = 413.97 - 29.47X + 0.54X^2 (R^2=0.670)$, wherein X=water temperature (° C.); or
      for the hormone treatment with the first injection of hCG followed by the second injection with the gonadoliberine in combination with the antidopaminergic agent:

$Y(hours) = 771.51 - 54.08X + 0.96X^2 (R^2=0.652)$, wherein X=water temperature (° C.),
   g) collecting sperm from the male spawners 10-48 h after hormone treatment, directly into a spermatozoid immobilization solution, and keeping the sperm at a cold temperature,
   h) in vitro fertilizing the eggs with said sperm,
   i) incubating the eggs under agitation at a temperature between 24-28° C. until hatching,
   j) collecting the hatched larvae, and
   k) raising the larvae until reaching a juvenile stage.

2. The method according to claim 1, wherein the fish are *Chromobotia macracanthus*.

3. The method according to claim 1, wherein the synthetic analogues of gonadoliberine are at least one of GnRHa and LHRH-A, and the antidopaminergic compound is at least one of domperidone and pimozide.

4. The method according to claim 3, wherein the GnRHa is selected from the group consisting of D-Arg6, Trp7, Leu8, Pro9, and Net.

5. The method according to claim 1, wherein the water which is used is recycled water circulating at a flow rate between 80%-100% renewal of the water per hour.

6. The method according to claim 1, wherein the water which is used has a pH between 7.0-8.0, a conductivity between 100-300 µS/cm, and an oxygen concentration between 6.0-8.0 mg/L.

7. The method according to claim 1, wherein i) incubating the eggs is carried out under agitation conditions comprising one of the following:
   agitating the eggs in a flow of water, said water having a flow rate between 0.3-2.3 L/min, or
   agitating the eggs in non-renewed water containers which are placed onto an oscillating tray oscillating at 56-88 oscillations per minute around an angle having a total amplitude of 10 degrees (+/−5 degrees).

* * * * *

UNITED STATES PATENT AND TRADEMARK OFFICE
CERTIFICATE OF CORRECTION

PATENT NO. : 8,701,596 B2  Page 1 of 1
APPLICATION NO. : 12/935288
DATED : April 22, 2014
INVENTOR(S) : Slembrouck et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 781 days.

Signed and Sealed this

Twenty-ninth Day of September, 2015

Michelle K. Lee
*Director of the United States Patent and Trademark Office*